United States Patent [19]
Johnson et al.

[11] Patent Number: 5,315,002
[45] Date of Patent: May 24, 1994

[54] SACCHARIDE MERCAPTALS

[75] Inventors: Trevor Johnson, Frodsham; Robert A. C. Rennie, Appleton, both of England

[73] Assignee: Imperial Chemical Industries PLC, London, England

[21] Appl. No.: 8,872

[22] Filed: Jan. 25, 1993

Related U.S. Application Data

[63] Continuation of Ser. No. 885,843, May 20, 1992, abandoned.

[30] Foreign Application Priority Data

May 31, 1991 [GB] United Kingdom ............... 9111758

[51] Int. Cl.$^5$ .......................... C07H 1/00; C08B 37/00
[52] U.S. Cl. ................................. 536/122; 536/17.5; 536/54; 536/124
[58] Field of Search ................ 536/17.5, 54, 122, 124

[56] References Cited

U.S. PATENT DOCUMENTS 3,635,717  1/1972  Ohi ..................................... 96/107

OTHER PUBLICATIONS

Jager et al, The stepwise degradation of a glycosylated aldose. A potential method for sequencing branched oligosaccharides, Carbohydrate Research, vol. 217, 18 Sep. 1991, pp. 99–106.

Gorin, The configuration of Glycosidic Linkages in Oligosaccharides, Canadian Journal of Chemistry, vol. 40, 1962, pp. 275–282.

Englmaier, High Resolution-GLC of Carbohydrates as their Dithioacetal-Trimethylsilylates and Trifluoroacetates, Journal of High Resolution Chromatography, vol. 13, No. 2, 1990, pp. 121–125.

Primary Examiner—Ronald W. Griffin
Attorney, Agent, or Firm—Cushman, Darby & Cushman

[57] ABSTRACT

Process for the preparation of a mercaptal of an oligosaccharide which process comprises the step of reacting the oligosaccharide with a thiol in the presence of an aqueous halocarboxylic or halosulphonic acid.

10 Claims, No Drawings

SACCHARIDE MERCAPTALS

This is a division of application Ser. No. 07/885,843, filed on May 20, 1992, now abandoned.

The present invention relates to a process for the preparation of mercaptals of oligosaccharides, particularly of disaccharides.

It is known that mercaptals of monosaccharides, e.g. D-glucose ethyl mercaptal, can be prepared in good yield by the concentrated hydrochloric acid catalysed reaction of a monosaccharide and the appropriate thiol (E. Fischer, Ber., 1894, 27, 673).

It has been reported that the diethyl mercaptal of maltose has been prepared in low yield by the reaction of the appropriate precursors in concentrated hydrochloric acid and isolated by conversion into an acetylated derivative thereof (M. L. Wolfrom, J.Am. Chem. Soc., 1931, 51, 4379).

Surprisingly, in the light of the known capability of aqueous trifluoroacetic acid mixtures to act as effective hydrolysis agents on oligo- and poly-saccharides, we have now devised a method by which mercaptals of oligosaccharides can be prepared.

According to the present invention there is provided a process for the preparation of a mercaptal of an oligosaccharide which process comprises the step of reacting the oligosaccharide with a thiol in the presence of a halocarboxylic or halosulphonic acid.

As examples of suitable thiols which may be used in the process according to the present invention may be mentioned inter alia hydrocarbyl thiols, e.g. aromatic thiols or preferably aliphatic thiols, more preferably $C_{1-8}$ thiols. We do not exclude the possibility that the thiol may bear one or more substituents which do not impede unduly the process of the present invention, e.g. a hydroxy substituent. A di-thiol may be used.

As examples of oligosaccharides which may be used in the process according to the present invention may be mentioned inter alia dextrin, maltotriose, maltohexose and corn syrup oligosaccharides, or preferably disaccharides, e.g. lactose, maltose, or cellobiose.

As examples of halocarboxylic acids and halosulphonic acids for use in the process of the present invention may be mentioned inter alia fluorosulphonic acids, perfluorosulphonic acids or preferably fluorocarboxylic acids, more preferably trifluoroacetic acid.

The halocarboxylic or halosulphonic acid used in the process according to the present invention may be neat acid or provide the major component of an aqueous mixture by volume, i.e. more than 50% v/v. Preferably the reaction is carried out in an acid/water mixture comprising between 70:30 by volume acid:water to 90:10 by volume acid:water.

Typically, the process according to the present invention is carried out at between 0° C. and 40° C., preferably at about 20° C., for between 1-18 hours.

Depending on the particular oligosaccharide and thiol used in the process according to the present invention, the skilled man will find by simple experiment suitable reaction conditions, e.g. acid concentration, temperature and time, for carrying it out.

The mercaptal product can be readily isolated from the reaction mixture by evaporation of the acid, preferably under reduced pressure or as an azeotrope with water. Alternatively, it may be isolated by solvent extraction to afford an aqueous solution or dispersion, from which the anhydrous product may be obtained by conventional methods.

According to a further aspect of the present invention there is provided a mercaptal of an oligosaccharide of the General Formula I

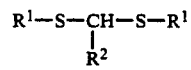

$$R^1-S-CH-S-R^1 \quad\quad I$$
$$\;\;\;\;\;\;\;\;\;\;\;\;|$$
$$\;\;\;\;\;\;\;\;\;\;\;R^2$$

with the proviso that it does not represent the diethyl mercaptal of maltose.

In General Formula I, each $R^1$, which may be the same or different, is a hydrocarbyl group, a substituted derivative thereof, or together form a ring structure with the $-S-CHR^2-S-$ moiety; and the moiety $R^2CH$ is derived from an oligosaccharide.

As examples of $R^1$ in the General Formula I, where it is a hydrocarbyl group, may be mentioned inter alia alkyl, e.g. $C_{1-20}$; aryl, e.g. phenyl; and aralkyl, e.g. benzyl groups, or preferably an alkyl group having 1-8 carbon atoms.

As examples of $R^1$ in the General Formula I, where it is a derivative of a hydrocarbyl group, may be mentioned inter alia $-(CH_2CH_2O)_mR^3$ and $-(CH_2CH_2O-CO)_mR^3$ wherein $R^3$ is hydrogen or a hydrocarbyl group and m is 1-60.

As examples of $R^1$ in General Formula I, where together they form a ring structure with the $-S-CHR^2-S-$ moiety, may be mentioned cyclic mercaptals of General Formula II,

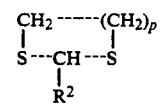

$$\;\;\;CH_2-----(CH_2)_p \quad\quad II$$
$$\;\;\;|\;\;\;\;\;\;\;\;\;\;\;\;\;|$$
$$S---CH---S$$
$$\;\;\;\;\;\;\;\;|$$
$$\;\;\;\;\;\;\;R^2$$

wherein p is 1 or 2.

In General Formula I, $R^1$ is preferably an alkyl group of $C_{1-18}$, more preferably $C_{1-8}$.

As examples of the moiety $R^2CH$ in General Formula I may be mentioned inter alia oligosaccharides, e.g. dextrin; or preferably disaccharides, e.g. lactose, maltose, cellobiose;

We do not exclude the possibility that $R^2$ in the General Formula I may bear one or more substituents $R^1$.

The present invention is further illustrated by reference to the following Examples.

EXAMPLE 1

This Example illustrates a mercaptal of an oligosaccharide and the preparation thereof by the process according to the present invention.

Methanethiol (16 cm³, 0.3 mol) was added, as a gas, with stirring to a suspension of lactose monohydrate (50 g, 0.14 mol) in trifluoroacetic acid (108 cm³) and water (12 cm³) at 0° C. over 20 minutes. The suspension was stirred at 20°-25° C. for 4½ hours. The resulting solution was concentrated under reduced pressure at 35° C. leaving a syrup which was co-evaporated twice with water (50 cm³). The resulting foam was triturated with ethyl acetate (200 cm³). The resulting white solid was collected by filtration then dried yielding 56.5 g (97%). The product was shown to be homogeneous by TLC (using silica gel plates, detected by sulphuric acid charring at 180° C. for 15 minutes), Rf 0.21 (12:3:1 ethyl acetate: methanol:water). The structure of the product was confirmed by Mass Spectrometry (Electron impact), principal fragment ions: mass of 107 ($CH_3S$—CH—$SCH_3$), mass of 295 (parent ion— HO—CH—CH($SCH_3$)$_2$), mass of 163 (Galactose residue). H NMR ($D_2O$,500 mHz) revealed characteristic signals (ppm), 2.4 (two singlets, 2×3H) 2[$CH_3$—S].

For further structural determination, a sample of the product was acetylated in pyridine using acetic anhydride at 0°-5° C. for 2 days. The solution was concentrated under reduced pressure at 35° C. leaving a gum which was purified by column chromatography using a silica gel column and 2:1 ethyl acetate: hexane as eluant. The product was homogeneous by TLC, Rf 0.4 (1:1 ethyl acetate:hexane). The structure was confirmed to be the octa-acetate derivative (thus confirming that lactose had not been hydrolysed) by $^1$H NMR (CDCl$_3$, 500 MHz), characteristic signals (ppm), 2.0 (singlet 6H) [2×$CH_3S$], 2.15-1.9 (8 singlets, 24H)

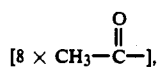

5.2-3.8 (14 multiplets, 14H) [14×CH—O]. Elemental analysis found: C 47.70%, H 6.17%; calculated for $C_{30}H_{44}O_{18}S_2$: C 47.61%, H 5.86%. It was found to have $[\alpha]^{20}_D$+22.2 (C=3 in CHCl$_3$).

EXAMPLES 2-8

These Examples illustrate further mercaptals and the preparation thereof by the process according to the present invention.

The procedure described in Example 1 was repeated except that the sugar/thiol combinations and reaction times shown in Table 1 were used instead of lactose/methanethiol and 4½ hours.

TABLE 1

| Example No | Sugar | Thiol | Reaction Time (hrs) | Yield % |
|---|---|---|---|---|
| 2 | Lactose | Butane | 22 | 98 |
| 3 | " | Hexane | 2 | 65 |
| 4 | " | Octane | 4 | 66 |
| 5 | Maltose | Methane | 4 | 96 |
| 6 | " | Hexane | 2 | 60 |
| 7 | " | Octane | 4 | 76 |
| 8 | Cellobiose | Hexane | 18 | 85 |

The products were analysed by NMR, MS and elemental analysis. The structures thereof were confirmed by conversion into the corresponding acetates.

The optical rotations of the products and the acetates prepared therefrom are shown in Table 2.

TABLE 2

| Example No | [α]$_D$ Product | [α]$_D$ Octa-acetate |
|---|---|---|
| 2 | +9.2<br>C = 0.98 in X | +34.8<br>C = 3.54 in Z |
| 3 | +8.8<br>C = 1.2 in X | +28.6<br>C = 3.5 in Z |
| 4 | +9.2<br>C = 1 in X | +34.1<br>C = 1 in Z |
| 5 | +75.3<br>C = 1.58 in Y | +80.1<br>C = 2.96 in Z |
| 6 | +76.5<br>C = 1 in X | +85.1<br>C = 2.96 in Z |
| 7 | +67.5<br>C = 1.25 in X | +81.3<br>C = 3 in Z |
| 8 | +14.2<br>C = 1.18 in X | +20.9<br>C = 2.44 in Z |

X: Methanol; Y: Water; Z: Chloroform

We claim:

1. A process for the preparation of a mercaptal of an oligosaccharide which process comprises the step of reacting the oligosaccharide with a thiol in the presence of a halocarboxylic or halosulphonic acid wherein the halocarboxylic acid or halosulphonic acid is neat acid or provides more than 50% v/v of an aqueous reaction mixture.

2. A process as claimed in claim 1 wherein the thiol is an aliphatic thiol.

3. A process as claimed in claim 2 wherein the aliphatic thiol bears 1-8 carbon atoms.

4. A process as claimed in claim 3 wherein the aliphatic thiol is methane, butane, hexane or octane thiol.

5. A process as claimed in claim 1 wherein the oligosaccharide is a disaccharide.

6. A process as claimed in claim 5 wherein the disaccharide is lactose, maltose or cellobiose.

7. A process as claimed in claim 1 wherein the halocarboxylic or halosulphonic acid is trifluoroacetic acid.

8. A process as claimed in claim 1 wherein the halocarboxylic or halosulphonic acid is present as an aqueous mixture which comprises between 70:30 by volume acid:water and 90:10 by volume acid:water.

9. A process as claimed in claim 1 carried out at about 20° C.

10. A mercaptal of a disaccharide of the formula

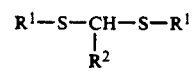

wherein
each $R^1$, which may be the same or different, is a methyl, butyl, hexyl or octyl group, a substituted hydrocarbyl group or together form a ring structure with the —S—$CHR^2$—S— moiety; and
the moiety $R^2$ —CH— is derived from lactose, maltose or cellobiose.

* * * * *